(12) United States Patent
Jorquera Nieto et al.

(10) Patent No.: US 10,350,274 B2
(45) Date of Patent: Jul. 16, 2019

(54) METHOD FOR THE PREPARATION OF HUMAN ALBUMIN WITH REDUCED LEVEL OF DISSOLVED OXYGEN

(71) Applicant: Grifols, S.A., Barcelona (ES)

(72) Inventors: Juan Ignacio Jorquera Nieto, Barcelona (ES); Ana Maria Ortiz Fernandez, Barcelona (ES); Montserrat Costa Rierola, Barcelona (ES)

(73) Assignee: GRIFOLS, S.A., Barcelona (ES)

( * ) Notice: Subject to any disclaimer, the term of this patent is extended or adjusted under 35 U.S.C. 154(b) by 199 days.

(21) Appl. No.: 14/724,649

(22) Filed: May 28, 2015

(65) Prior Publication Data

US 2015/0343025 A1 Dec. 3, 2015
US 2017/0000855 A9 Jan. 5, 2017

(30) Foreign Application Priority Data

May 29, 2014 (ES) .................................. 201430824

(51) Int. Cl.
| | |
|---|---|
| *A61K 38/38* | (2006.01) |
| *A61K 9/08* | (2006.01) |
| *A61K 47/02* | (2006.01) |
| *A61K 47/08* | (2006.01) |
| *A61K 9/00* | (2006.01) |

(52) U.S. Cl.
CPC ............ *A61K 38/38* (2013.01); *A61K 9/0019* (2013.01); *A61K 47/02* (2013.01)

(58) Field of Classification Search
CPC ....... A61K 38/38; A61K 9/0019; A61K 47/02
See application file for complete search history.

(56) References Cited

U.S. PATENT DOCUMENTS

| | | | |
|---|---|---|---|
| 4,094,965 A | 6/1978 | Layne et al. | |
| 8,231,599 B2 * | 7/2012 | Jorquera Nieto | C07K 14/765 424/529 |
| 2002/0192411 A1 | 12/2002 | Kai et al. | |

FOREIGN PATENT DOCUMENTS

| | | |
|---|---|---|
| EP | 1 538 151 A1 | 6/2005 |
| WO | WO 2003020325 A2 | 3/2003 |

OTHER PUBLICATIONS

Akers, M.J., et al. 2012 Pharmaceutical Formulation Development of Peptides and Proteins 2nd edition, Hovgaard et al., chapter 8: p. 149, 158-162.*
Butler, I.B., et al. 1994 Talanta 41(2): 211-215.*
Peters, Jr., T., "All About Albumin Biochemistry, Genetics and Medical Applications," Copyright © 1995 Elsevier Inc., ISBN: 978-0-12-552110-9 (Abstract Only).
Otagiri M., Chuang V.T. Pharmaceutically important pre- and posttranslational modifications on human serum albumin. Biol Pharm Bull 32:527-534, 2009.
Oettl K., et al. Oxidative damage of albumin in advanced liver disease. Biochim. Biophys. Acta 1782: 469-473, 2008.
Oettl K. and Marsche G. Redox State of human serum albumin in terms of cysteine-34 in health and disease. Methods Enzymol. 474:181-95, 2010.
Oettl K. et al. Oxidative albumin damage in chronic liver failure: Relation to albumin binding capacity; liver dysfunction and survival. J Hepatol 59:978-983, 2013.
Cohn E.J. et al. Preparation and properties of serum plasma proteins, IV. A system for the separation into fractions of the protein and lipoprotein components of biological tissues and fluids. J. Am. Chem. Soc. 68, 459-475, 1946.
Akers, M. J. & Defelippis, M. R. Peptides and proteins as parenteral solutions. En: Pharmaceutical formulation development of peptides and proteins. USA, Edited by Hovgaard, L., Frokjaer, S., van de Weert, M. Taylor & Francis Group., Second edition, 2012, Chapter 8, pp. 161-162, ISBN 978-1-4398-5388-7.
Hayashi, T. et al. The importance of sample preservation temperature for analysis of the redox state of human serum albumin. Clinica Chimica Acta. vol. 316, pp. 175-178, Feb. 2002.
Marie, A.-L. et al. Capillary zone electrophoresis and capillary electrophoresis-mass spectrometry for analyzing qualitative and quantitative variations in therapeutic albumin. Analytica Chimica Acta. vol. 800, pp. 103-110, Oct. 2013.
Search Report for ES201430824 dated Nov. 18, 2014.
Extended European Search Report dated Nov. 9, 2015 issued in European Application No. 15382164.0-1456.
Oettl et al., "Physiological and pathological changes in the redox state of the suman serum albumin critically influence its binding properties," 2007, British Journal of Pharmacology, vol. 151, No. 5, pp. 580-590.

* cited by examiner

*Primary Examiner* — Marsha Tsay
(74) *Attorney, Agent, or Firm* — Knobbe, Martens, Olson & Bear, LLP (57) ABSTRACT

A method prepares a solution of human albumin by reducing dissolved oxygen in a solution of albumin until a concentration of oxygen equal to or less than 0.5 ppm is achieved. A solution of human albumin having a redox state closer to the redox state of the albumin present in human plasma can be achieved.

11 Claims, 7 Drawing Sheets

METHOD FOR THE PREPARATION OF HUMAN ALBUMIN WITH REDUCED LEVEL OF DISSOLVED OXYGEN

FIELD OF THE INVENTION

The present invention relates to a method for the preparation of a solution of human albumin, more particularly it relates to a method comprising a stage of reducing the dissolved oxygen in said solution of albumin until a concentration equal to or less than 0.5 ppm. With the method of the present invention it is possible to obtain a solution of human albumin having a redox state closer to the redox state of the albumin present in human plasma.

SUMMARY

A method of preparing a solution of a human albumin includes a stage of reducing a level of dissolved oxygen in the solution, wherein the level of dissolved oxygen is reduced to a concentration equal to or less than 0.5 ppm.

The stage of reducing the level of dissolved oxygen in the solution can be carried out by a surface treatment of the solution with an inert gas or by bubbling of an inert gas into an interior of the solution.

The human albumin can be of any origin, such as a plasmatic recombinant origin or a transgenic origin.

An exemplary concentration of the human albumin would be between about 4% and 25% (w/v).

Examples of the inert gas include nitrogen or helium.

The stage of reducing the level of dissolved oxygen in the solution is sometimes carried out prior to or subsequent to a stage of pasteurisation of the solution.

The solution can be maintained in an inert gas atmosphere, including a gas such as nitrogen or helium, subsequent to the stage of reducing the level of dissolved oxygen in the solution.

The solution can be packed and/or stored in a container including a material impermeable to oxygen, such as glass.

An exemplary concentration of dissolved oxygen would be equal to or less than 0.5 ppm.

The solution can be prepared into a medicament.

BRIEF DESCRIPTION OF THE DRAWINGS

FIG. 2 shows a graph of the concentration of the HMA, HNA1 and HNA2 forms of Cys-34 of the albumin expressed as the height of the peak obtained by means of chromatography in various stages of the method utilised in the state of the art prior to the present invention: (□) plasma from healthy donors (n=59); (★) supernatant from cryoprecipitation (n=3); (⊗) solution of albumin prior to addition of stabilisers and prior to heat treatment (n=3); (●) solution of albumin with stabilisers and prior to heat treatment (n=1); (■) solution of albumin with stabilisers and subsequent to heat treatment (n=1); (◆) 20% solution of albumin prior to sterile filtration (n=3); (▲) sterile 20% albumin solution and in final container (n=4); (▼) pasteurised 20% albumin solution in final container and unquarantined (n=4); and (○) final 20% albumin product (n=7); wherein n represents the number of analysed batches.

DETAILED DESCRIPTION

Human albumin is a non-glycosylated protein of 66 kDa. Quantitatively, it is the most significant plasma protein and the concentration thereof in normal plasma lies between 35 and 50 g/l, constituting up to 60% of total plasmatic proteins (Peters T. J.: All About Albumin; Biochemistry, Genetics and Medical Applications. Academic Press, San Diego, 1996).

The structure of human albumin consists of a polypeptide having 585 amino acids with about 67% alpha-helices, without beta-sheets being present (Otagiri M., Chuang V. T.:

Pharmaceutically important pre- and posttranslational modifications on human serum albumin. Biol Pharm Bull 2009; 32:527-534). Human albumin contains methionine and 35 cysteine residues involved in the formation of 17 disulphide bonds. Cys-34 is the only free cysteine in the entire molecule. Human albumin has specific antioxidant functions by virtue of the capacity to bond to multiple ligands and the radical entrapment properties thereof, both closely related to the structure thereof.

Although many possibilities of oxidation of albumin exist, Cys-34 is a site particularly sensitive to oxidation/reduction. Consequently, in general, it is legitimate to speak of the redox state of albumin in terms of Cys-34. Through the chromatographic separation of albumin, three fractions are obtained, according to the redox state of Cys-34 (Peters, 1996, op. cit.):

(i) the reduced form wherein the cysteine is in the form of a free thiol group, referred to as human mercaptoalbumin (HMA);
(ii) the oxidised form wherein the cysteine forms a disulphide bond with a small thiol compound, principally cysteine or cysteinylglycine, although also with homocystein and glutathione, referred to as human non-mercaptoalbumin 1 (HNA1); and
(iii) the most oxidised form wherein the cysteine is sulphinic or sulphonic acid, referred to as human non-mercaptoalbumin 2 (HNA2).

In a healthy person, about 50-69% of the total albumin is in the form of HMA, 27-42% in the form of HNA1, and 3-5% in the form of HNA2 (Oettl K., et al. Oxidative damage of albumin in advanced liver disease. Biochim. Biophys. Acta 2008; 1782: 469-473; Oettl K. and Marsche G. Redox State of human serum albumin in terms of cysteine-34 in health and disease. Methods Enzymol. 2010; 474:181-95; and Oettl K. et al. Oxidative albumin damage in chronic liver failure: Relation to albumin binding capacity; liver dysfunction and survival. J Hepatol, 2013, 59:978-983). In general it is believed that the oxidation of HMA to HNA1 is reversible, whereas oxidation to HNA2 is an irreversible process.

Albumin may undergo diverse structural modifications, both in vivo and during the methods employed to produce therapeutic albumin, resulting in the modification of the conformation thereof and, as a consequence, the bonding properties together with the redox state thereof (Oettl, K. et al, 2010, op. cit.).

The commonly used method in the fractionation of human plasma for the obtainment of the purified proteins, among which is to be found albumin, is the Cohn method (Cohn E. J. et al. 'Preparation and properties of serum plasma proteins, IV. A system for the separation into fractions of the protein and lipoprotein components of biological tissues and fluids. J. Am. Chem. Soc. (1946) 68, 459-475), or minor modifications thereof.

The Cohn method commences with human plasma which is subjected to successive stages of precipitation and separation. In each a precipitate enriched in one of the plasmatic proteins and a decantation supernatant is obtained. To achieve the precipitation of the successive Cohn fractions (Fraction I, Fraction II+III, Fraction IV and Fraction V) it is necessary to modify parameters of the solution with the objective of varying the solubility of the different proteins, such as, inter alia, pH, dielectric constant, temperature, protein concentration, and ionic strength. It should be pointed out, additionally, that said Cohn fractions contain increasing concentrations of ethanol. As a consequence, the albumin contained in the supernatant of Fraction IV is precipitated with about 40% (v/v) ethanol and goes on to form part of the paste of Fraction V.

Once Fraction V is obtained, the latter is resuspended in a solution and is subjected to different stages until the final product is obtained. Habitually, these stages include: diafiltration, heat treatment, sterilisation, filling into vials, and final pasteurisation of said vials, prior to submission of said vials to quarantine, in general during a period of not less than 14 days at 30-32° C., with the objective of ensuring the sterility of the final product.

The present inventors have discovered that during the process of obtainment of a solution of albumin commencing from human plasma the albumin suffers modifications to the redox state of Cys-34. These modifications occur fundamentally during storage in the presence of oxygen, by virtue whereof they are essentially detected following the quarantine stage. In several production batches (n=7) it has been found that the levels of HMA, HNA1 and HNA2 are 40-53%, 39-44% and 7-16% (w/v), respectively and, as a consequence, principally the levels of HMA and HNA2 differ from those described in healthy persons (Oettl K. 2008, 2010 and 2013, ops. cit.). This may be of significant importance, for example in the case of HNA2, by virtue of the fact that oxidation to HNA2 is an irreversible process, as hereinbefore stated.

Surprisingly, the inventors have discovered that, by means of the addition of a stage in the process of production of a solution of human albumin comprising reducing the dissolved oxygen in the solution, wherein the level of oxygen is reduced to a concentration equal to or less than 0.5 ppm, a reduction in the oxidation of Cys-34 is achieved, there being obtained a redox state of the albumin very similar to the redox state which albumin presents in blood plasma. This results in the fact that the properties of the obtained albumin, for example the antioxidant properties thereof, are more similar to those of the albumin present in blood, which may give rise to an improvement in the therapeutic efficacy thereof in many of the applications thereof.

Consequently, the present invention reveals a method for the preparation of a solution of human albumin characterised in that it comprises a stage of reducing the dissolved oxygen in said solution of albumin, wherein the level of oxygen is reduced to a concentration equal to or less than 0.5 ppm. Preferably, subsequent to the stage of reducing the dissolved oxygen in the solution of albumin, said solution of albumin is maintained in an inert gas atmosphere.

Said stage of reducing the dissolved oxygen in the solution of albumin may be carried out in various ways known in the state of the art. Preferably, a surface treatment of the solution of albumin may be realised with an inert gas or an inert gas may be bubbled into the interior of said solution of albumin. Said inert gas used in the method of the present invention may be nitrogen, helium or similar gases.

The method of the present invention may be utilised for the obtainment of solutions of albumin having an albumin concentration of between about 4 and 25% (w/v). Preferably, the obtained albumin is therapeutic albumin.

Furthermore, the albumin of the present invention may be albumin obtained in recombinant or transgenic form. The molecule of recombinant or transgenic albumin is identical to human albumin in terms of the sequence of amino acids thereof, it does not present glycosylation and, having the objective of it being functional, it must present the same conformational folding as the albumin of human plasmatic origin. Should this not be so it could not be administered to humans by virtue of the risk of immunogenicity, among other possible adverse effects caused by said differences.

The stage of reducing the dissolved oxygen in the solution of albumin of the present invention may be carried out prior to or subsequent to a stage of pasteurisation of said solution of albumin, or moreover it may be carried out although a stage of pasteurisation of said solution of albumin is not realised, being independent of the process of preparation of the initial solution of albumin.

To obtain better results in terms of the redox state of Cys-34 in the solution of albumin obtained by means of the method of the present invention, preferably subsequent to the stage of reducing the dissolved oxygen in the solution of albumin, said solution of albumin is maintained in an inert gas atmosphere. Said inert gas atmosphere may be of nitrogen, helium or similar gases.

Although it is possible to utilise any container of those wherein the albumin obtained by means of the method of the present invention is packed and/or stored, it is preferable that said container is manufactured from a material impermeable to oxygen, more preferably from glass.

A further objective of the present invention is to reveal a composition comprising human albumin prepared by means of the method of the present invention and the use thereof as medicament.

Finally, the present invention reveals the use of a composition comprising albumin prepared according to the hereinbefore described method for the preparation of a medicament.

The present invention is described below in greater detail in relation to examples and comparative examples not constituting a limitation of the invention. Furthermore, reference is made to the figures disclosed herein.

EXAMPLES

Figure 1:
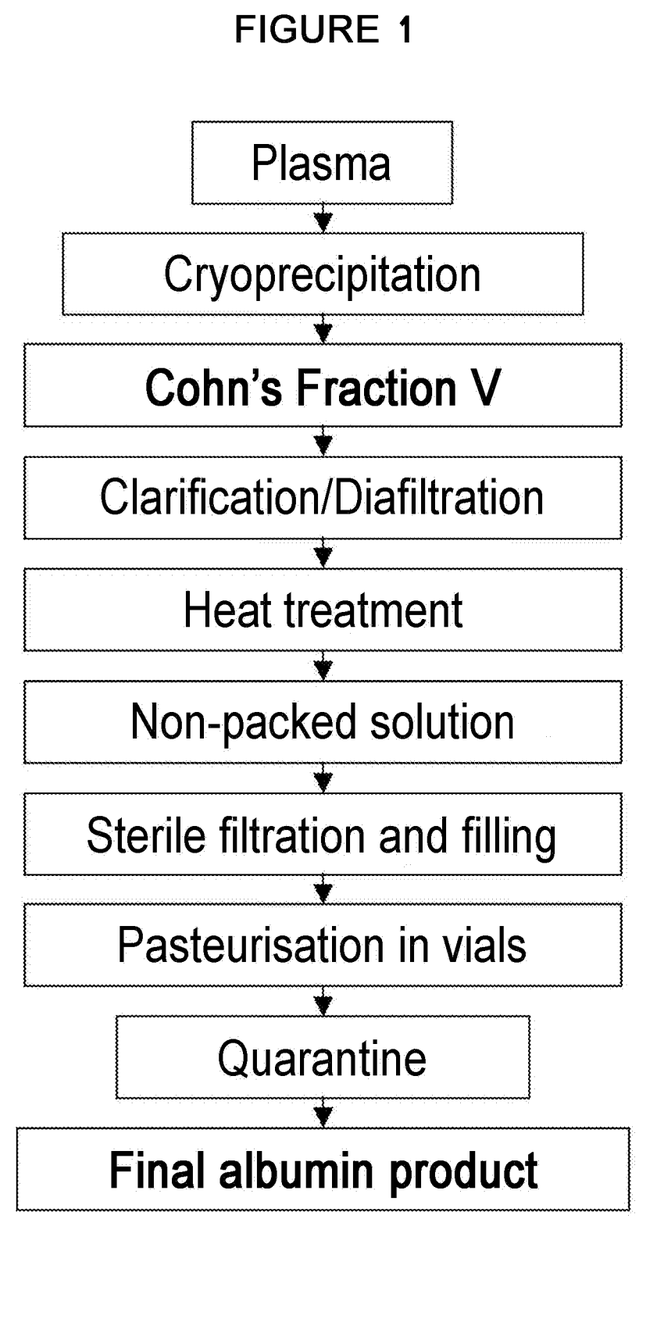
FIG. 1 shows a schematic diagram of a method for the obtainment of therapeutic human albumin from plasma utilised in the prior state of the art.

Example 1: Method for the Obtainment of Albumin According to the Prior State of the Art Human plasma obtained from healthy donors was subjected to successive stages of precipitation and separation, according to Cohn's method (Cohn E. J. et al, 1946, op. cit.), from the obtainment of the initial cryoprecipitation supernatant until achieving the precipitation of Fraction V (see FIG. 1). Cohn's Fraction V was suspended in cold water for injection (WFI), it was adjusted to pH 7.0 and was clarified by means of in-depth filters. The clarified solution was diafiltered at constant volume, applying a dialysis solution formed by a salt of monovalent ions (sodium chloride) and maintaining the temperature at 5° C. (FIG. 1, clarification/diafiltration stage). Sodium caprylate and N-acetyltryptophan were added as stabilisers to the diafiltered solution. Said solution was subjected to heat treatment at 60° C. (FIG. 1, heat-treatment stage). Subsequently the heat-treated solution was diluted with WFI or was concentrated as a function of the desired final protein concentration desired (for example, 5%, 20% or 25% (w/v)) (FIG. 1, non-packed solution). The final solution was then filtered in a sterile manner (0.22 μm filters) and the filling of the final sterile containers was proceeded to in an aseptic zone (FIG. 1, sterile filtration and filling stage). The solution in the final container was heated at 60° C. during not less than 10 h (FIG. 1, pasteurization in vials stage). Finally, the vials were incubated at 30-32° C. during not less than 14 days (FIG. 1, quarantine stage). Following said period, the vials were visually inspected to discard any indication of microbial contamination (FIG. 1, final albumin product).

The oxidative state of the samples of albumin from different stages of the process of obtainment of the albumin (FIG. 2) was analysed by high-performance liquid chromatography (HPLC), based on the method described by Oettl K., 2010, op. cit., and as detailed below.

The samples of albumin under study were diluted in a buffer of 0.3 M, sodium chloride, 0.1 M sodium phosphate, pH 6.87, to a concentration of 6.5 mg/ml, and 5 μl was injected into a Shodex Asahipak ES-502N DEAE anion exchange column (7.5×100 mm, Shodex, Japan) with a flow of 1.0 ml/min. The separation of the samples of albumin into three fractions (HMA, HNA1 and HNA2), according to the oxidative state thereof, was achieved following carrying out the elution thereof utilising a sodium acetate 50 mM and sodium sulphate 400 mM gradient, at a pH of 4.85, until attaining 6% ethanol at a constant flow of 1.0 ml/min at 35° C.

The 5 first minutes of elution were carried out in the absence of ethanol. In the following 5 to 35 minutes the concentration of ethanol was increased in a linear manner to 6%, subsequently maintaining it constant during a further 5 minutes. Finally, from minute 40 to 45, the concentration of ethanol was reduced again to 0%. After further 5 minutes without ethanol, the next sample could be analysed.

The detection of the three fractions of the albumin as a function of the oxidative state thereof was carried out by means of fluorescence, utilising as excitation and emission wavelengths 280 and 340 nm, respectively. The quantification of the concentration of the HMA, HNA1 and HNA2 forms of Cys-34 of the albumin was carried out taking into account the height of each of the peaks of interest obtained in the corresponding chromatogram.

Figure 2:
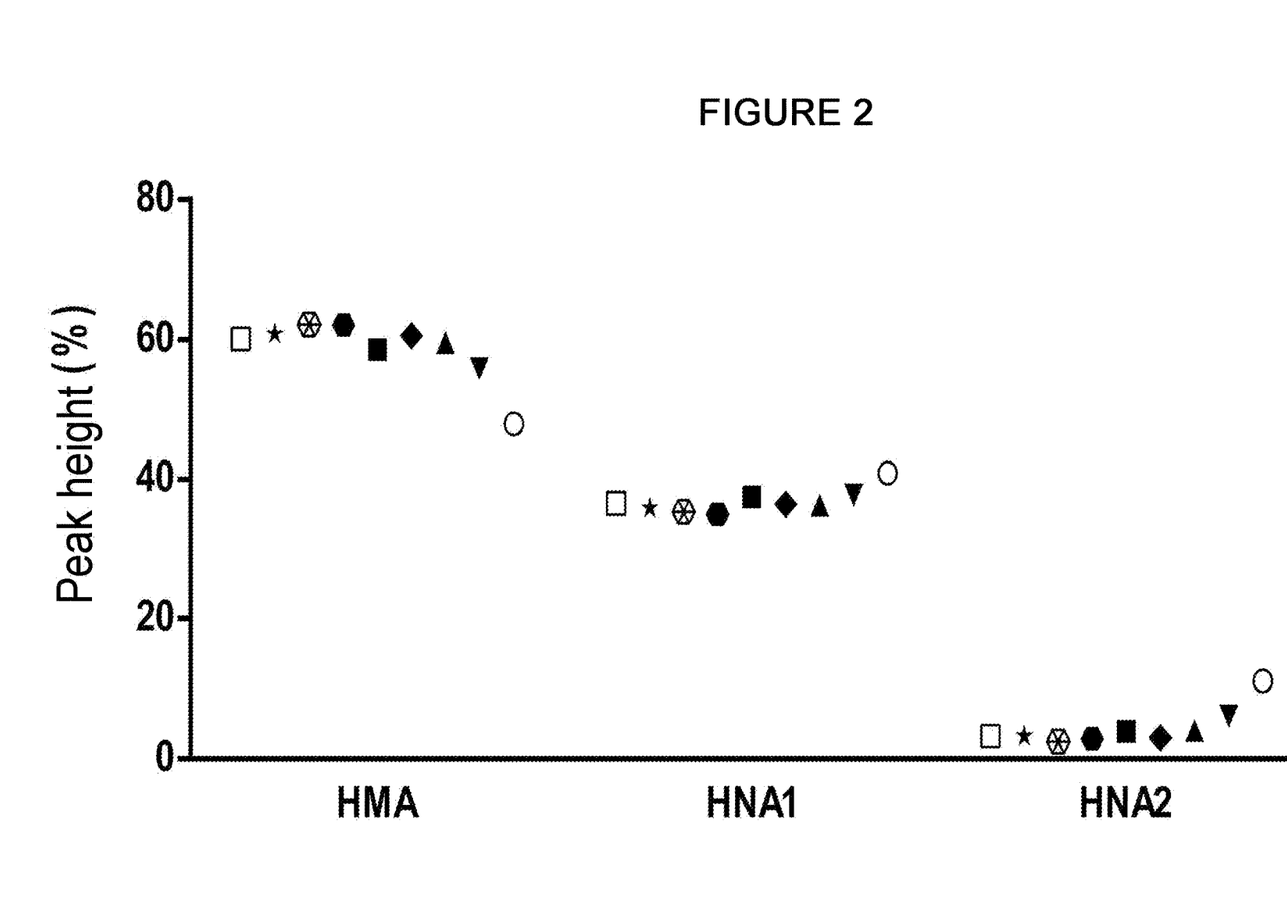
Figure 3:
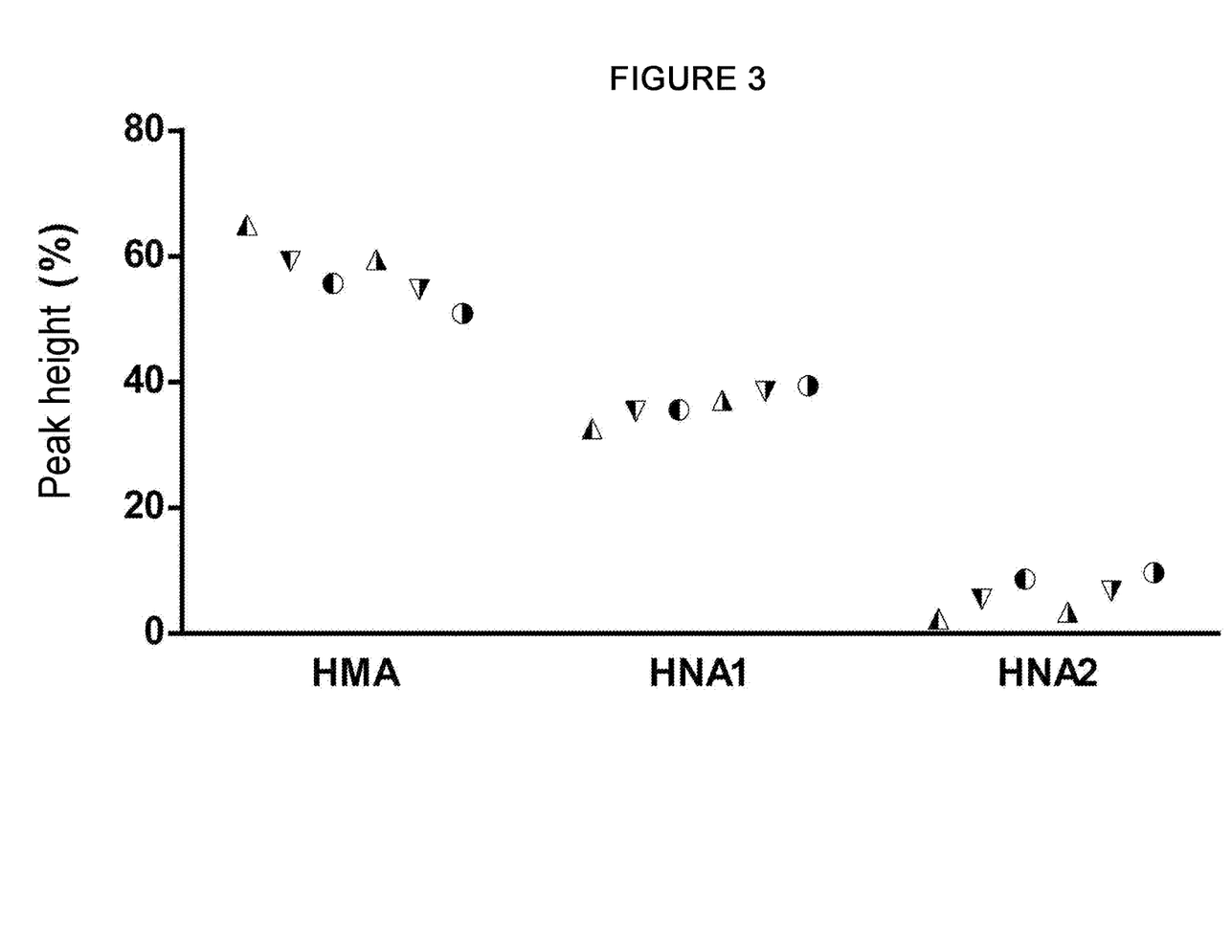
FIG. 3 shows a graph of the concentration of the HMA, HNA1 and HNA2 forms of Cys-34 of the albumin expressed as the height of the peak obtained by means of chromatography in various stages, utilising the method of the state of the art prior to the present invention: (▲) sterile 25% solution of albumin and in final container (n=1); (▼) pasteurised 25% solution of albumin unquarantined (n=1); and (●) 25% final albumin product (n=1); (▲) sterile 5% solution of albumin and in final container (n=1); (▼) pasteurised 5% solution of albumin in final container and unquarantined (n=1); and (●) final 5% albumin product (n=1); wherein n represents the number of analysed batches.

FIG. 2 shows the change in the oxidative state of the samples of human serum albumin from different stages during the process of obtainment of albumin of the prior state of the art. The data shows an increase in the HNA1 and HNA2 forms in detriment to the HMA form, particularly subsequent to the stage of pasteurisation with subsequent quarantine (final 20% albumin product). The behaviour of the oxidative state of the albumin following the stages of pasteurisation and quarantine in purified 5% and 25% albumin concentration from human plasma with the method of the prior state of the art (FIG. 3) is equivalent to that observed for the final 20% albumin products following the same technique (FIG. 2). In both figures the data obtained shows an increase in the HNA1 and HNA2 forms in detriment to the HMA form, particularly following the stage of pasteurisation with subsequent quarantine.

Example 2: Method for the Obtainment of Albumin of the Present Invention Utilising a Stage of Surface Treatment with Nitrogen Prior to the Pasteurisation The method for the obtainment of the albumin of the present invention corresponds to the method described in Example 1, further including a stage of reducing dissolved oxygen in the solution of albumin, as is described below.

Following the obtainment of the sterile solution in the final container (FIG. 1, sterile filtration and filling stage), and having the objective of displacing the oxygen present in the interior of the container, a surface treatment with nitrogen was carried out, inserting into the chlorobutyl stopper of the vial two hypodermic needles (of the commercial type Braun Sterican 21G×1½", 0.80×40 mm, Germany, or similar) connected to two 0.22 μm PVDF filters (of the commercial type Millex GV Millipore, 0.22 μm, PVDF, 13 mm filter, USA, or similar), avoiding contact of the needles with the solution of albumin. One of the needles was destined as the inlet of the nitrogen gas and the other as the outlet thereof having the objective of preventing overpressure within the container. The treatment with surface nitrogen was carried out at room temperature for two hours, maintaining a constant flow of nitrogen having the objective of permitting observation of the movement of the liquid within the container without its splashing within the same.

Figure 4:
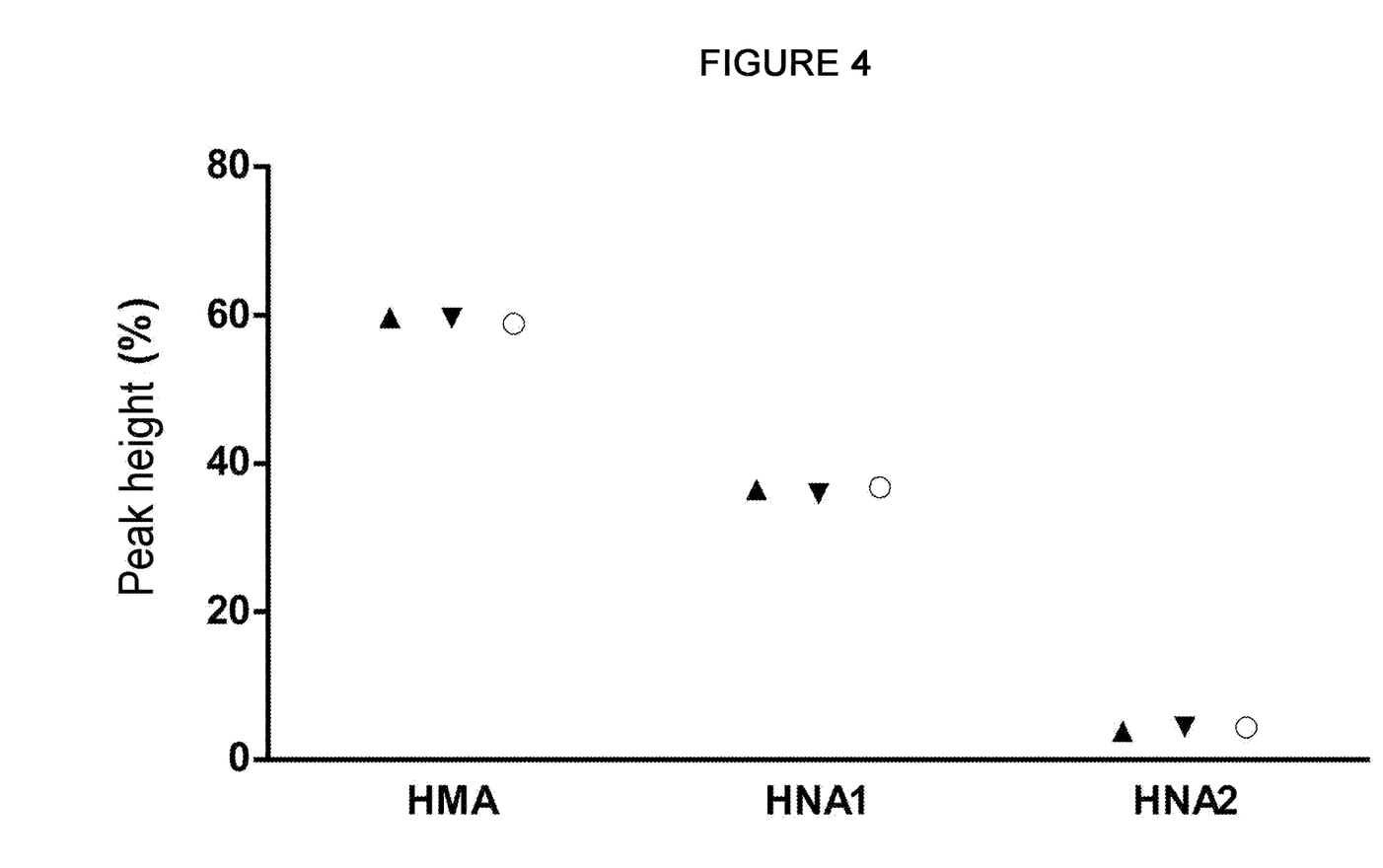
FIG. 4 shows a graph of the concentration of the HMA, HNA1 and HNA2 forms of Cys-34 of the albumin expressed as the height of the peak obtained by means of chromatography in various stages, utilising the method of the present invention wherein a stage of surface treatment with gaseous nitrogen prior to the pasteurisation was used: (▲) sterile 20% solution of albumin and in final container (n=3); (▼) pasteurised 20% solution of albumin in final container and unquarantined (n=3); and (○) final 20% albumin product (n=3); wherein represents the number of analysed batches.

Having completed the surface treatment with nitrogen, the method for the obtainment of albumin from human plasma continued as described in Example 1 (FIG. 1, pasteurization in vials stage), until the obtainment of the final albumin product. In the same manner as in Example 1, by means of anion exchange chromatography the oxidative state of the 20% concentration samples obtained with the technique of the present invention was analysed. Specifically, samples of albumin subjected to a stage of surface treatment with nitrogen prior to pasteurisation, samples of albumin following pasteurisation and prior to quarantine, and samples of albumin following the period of quarantine, were analysed. FIG. 4 shows the results obtained, there was observed the non-decrease in the HMA form and the non-increase in the HNA1 and HNA2 forms observed in FIGS. 2 and 3 with the method for the obtainment of the albumin of the prior art.

In addition to the analysis of the oxidative state, measurement of the dissolved oxygen present in the samples following the surface treatment with nitrogen was made, the result being that in all cases the concentration of dissolved oxygen was equal to or less than 0.5 ppm.

The determination was carried out at room temperature by means of the use of a probe for the measurement of dissolved oxygen (of the commercial type HI 9828 Multiparameter Meter, Hanna Instruments, USA). Specifically, the container with the solution of albumin previously subjected to the surface treatment with nitrogen was opened in the interior of a cubicle having a nitrogen atmosphere and the probe for the measurement of oxygen in the sample was immediately submerged. The employed probe, whose functioning is based on the principle of the galvanic cell, comprised a silver (Ag) anode sheathed with a platinum (Pt) wire functioning as cathode. The aforedescribed assembly is inserted in a protective cover full of an electrolytic solution of potassium chloride which has at its extremity a membrane of Teflon®, a material permeable to the gas, permitting the passage of the oxygen present in the solution but not the passage of the solution itself. By means of the application of a potential of 790 mV, the oxygen present in the cell is reduced to hydroxide ions ($OH^-$) at the cathode and silver chloride is deposited at the anode. This reaction brings about a current flow having an intensity proportional to the quantity of oxygen present in the sample. The meter then converts the measurement of the current flow into the corresponding concentration of dissolved oxygen.

Example 3: Method for the Obtainment of Albumin of the Present Invention Utilising a Stage of Bubbling Nitrogen into the Solution Prior to the Pasteurisation The method for the obtainment of the albumin of the present invention corresponds to the method described in Example 1, including the stage described below. Following the obtainment of the sterile solution in the final container (FIG. 1, sterile filtration and filling stage), and having the objective of displacing the oxygen present in the interior of the container, the treatment of bubbling nitrogen was carried out by inserting into the chlorobutyl stopper of the vial two hypodermic needles (of the commercial type Braun Sterican 21G×1½", 0.80×40 mm, Germany, or similar) connected to two 0.22 μm PVDF filters (of the commercial type Millex GV Millipore, 0.22 μm, PVDF, 13 mm filter, USA, or similar). The needle destined as the inlet of the nitrogen gas, a spinal needle (of the commercial type Terumo Spinal Needle, 18G×3½", 1.20×90 mm, Japan, or similar), was submerged in the solution of albumin and the hypodermic needle (of the commercial type Braun Sterican 21G×1½", 0.80×40 mm, Germany, or similar), located avoiding contact with the liquid, was destined as the outlet thereof having the objective of preventing overpressure within the container. The treatment of bubbling nitrogen was carried out at room temperature for two hours, maintaining a constant flow of nitrogen having the objective of permitting observation of small bubbles within the liquid.

Having completed the treatment of bubbling nitrogen, the method for the obtainment of albumin from human plasma continued as described in Example 1 (FIG. 1, pasteurization in vials stage), until the obtainment of the final albumin product.

Figure 5:
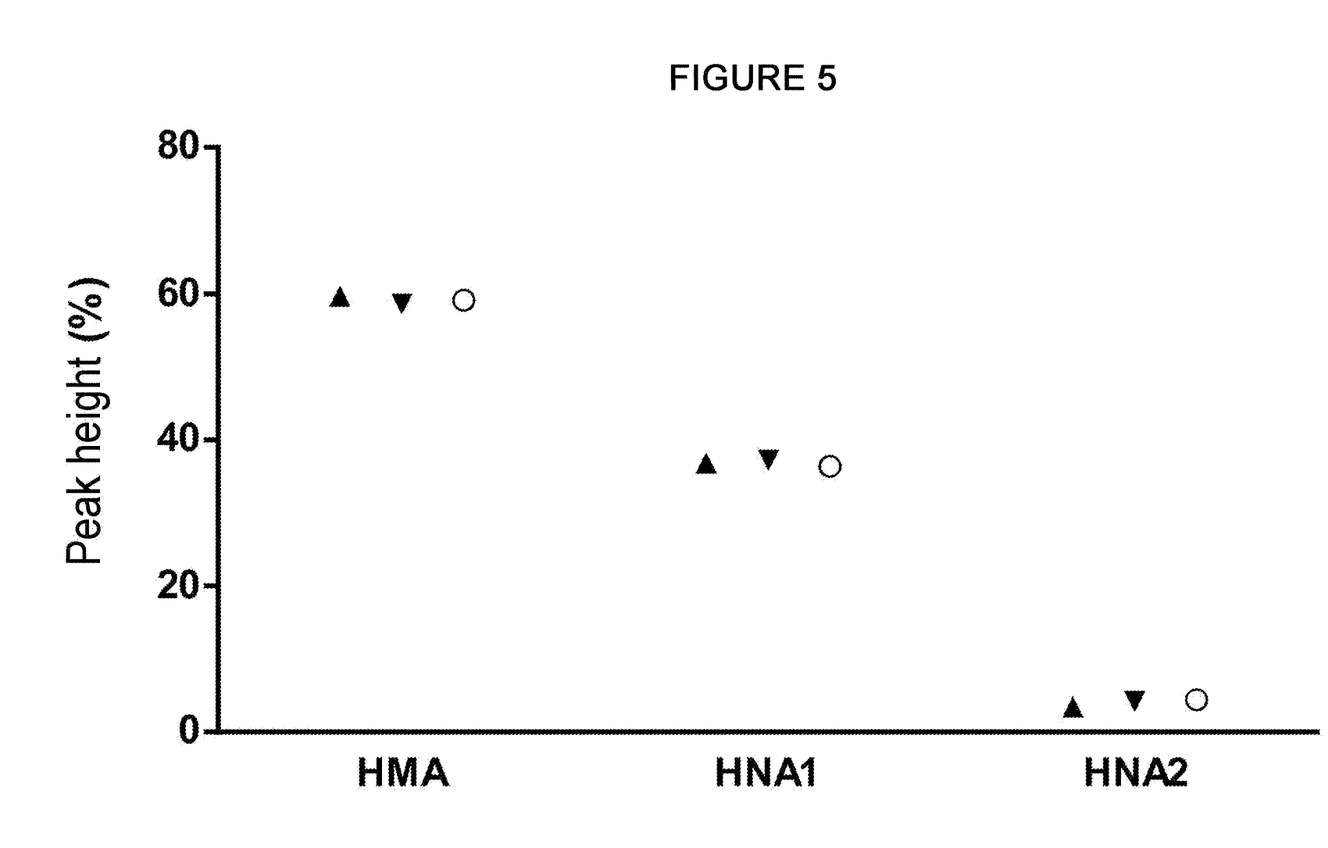
FIG. 5 shows a graph of the concentration of the HMA, HNA1 and HNA2 forms of Cys-34 of the albumin expressed as the height of the peak obtained by means of chromatography in various stages, utilising the method of the present invention wherein a stage of treatment of bubbling gaseous nitrogen into the solution of albumin prior to prior to the pasteurisation was used: (▲) sterile 20% solution of albumin and in final container (n=3); (▼) pasteurised 20% solution of albumin in final container and unquarantined (n=3); and (○) final 20% albumin product (n=3); wherein n represents the number of analysed batches.

In the same way as in Examples 1 and 2, the oxidative state was analysed by means of anion exchange chromatography of the samples of 20% albumin concentration obtained by the technique of the present invention. Specifically, samples of albumin subjected to a stage of bubbling nitrogen prior to the stage of pasteurisation, samples of albumin following the pasteurisation and prior to quarantine, and samples of albumin following the period of quarantine, were analysed. FIG. 5 shows the results obtained, these being similar to those obtained in FIG. 4, utilising a stage of surface treatment with nitrogen prior to the pasteurisation. There was observed the non-decrease in the HMA form and the non-increase in the HNA1 and HNA2 forms observed in FIGS. 2 and 3 with the method for the obtainment of albumin of the prior art.

In this case the measurement of the dissolved oxygen present in the samples following treatment of bubbling nitrogen was also carried out, in the same manner as in Example 2, the result being that in all cases the concentration of dissolved oxygen was equal to or less than 0.5 ppm.

Figure 6:
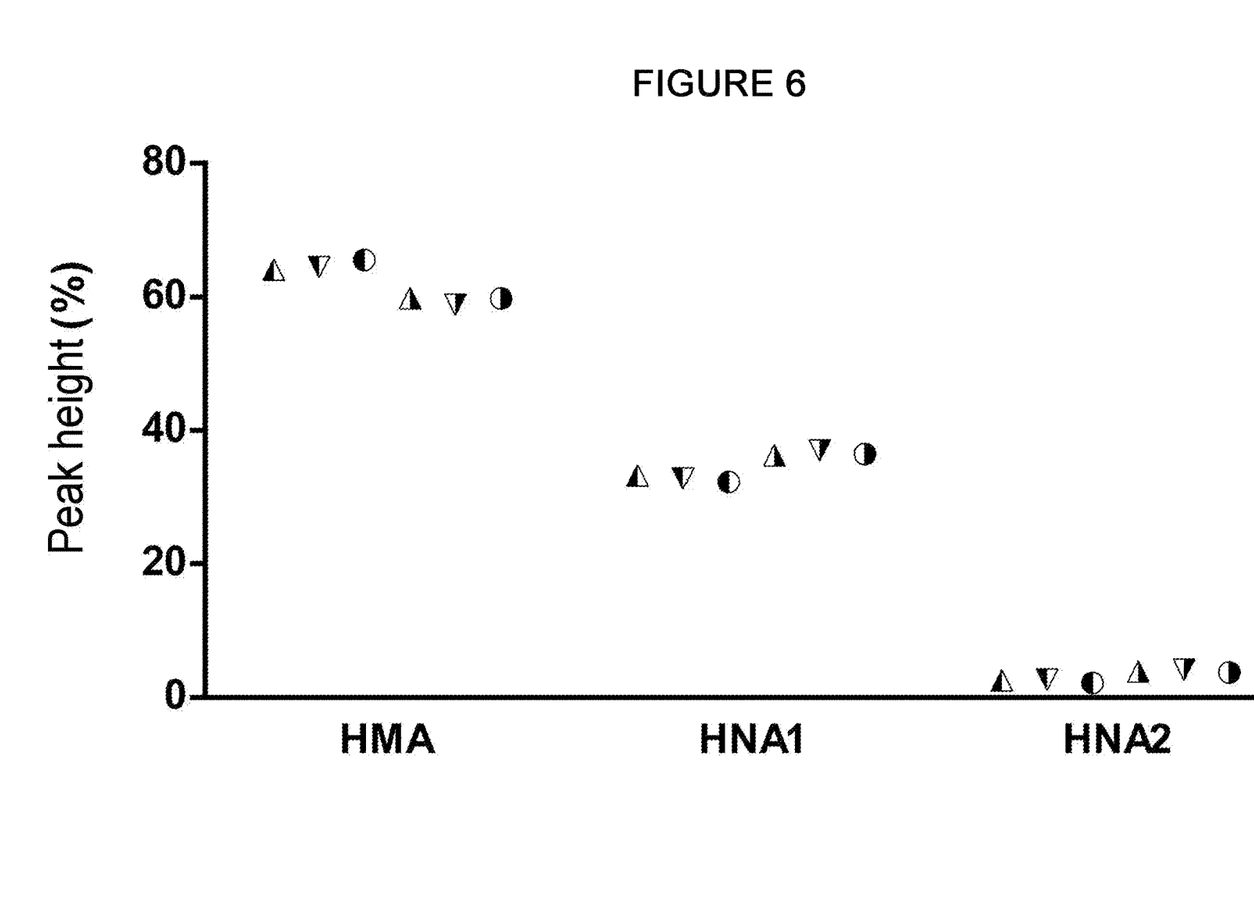
FIG. 6 shows a graph of the concentration of the HMA, HNA1 and HNA2 forms of Cys-34 of the albumin expressed as the height of the peak obtained by means of chromatography in various stages, utilising the method of the present invention wherein a stage of surface treatment with gaseous nitrogen prior to the pasteurisation was used: (▲) sterile 25% solution of albumin not packed (n=1); (▼) pasteurised 25% solution of albumin and unquarantined (n=1); and (●) final 25% albumin product (n=1); (▲) sterile 5% solution of albumin and in final container (n=1); (▼) pasteurised 5% solution of albumin in final container and unquarantined (n=1); and (●) final 5% albumin product (n=1); wherein n represents the number of analysed batches.

Example 4: Method for the Obtainment of Albumin of the Present Invention Utilising a Stage of Surface Treatment with Nitrogen Prior to the Pasteurisation, Applied to Different Final Concentrations of Albumin The method for the obtainment of the albumin of the present invention corresponds to the method described in Example 2, applied to other concentrations of albumin such as 5 and 25%. In the same manner as in Example 2, the oxidative state of the samples of 5 and 25% concentration of albumin obtained with the technique of the present invention was analysed by means of anion exchange chromatography. Specifically, samples of 5 and 25% albumin subjected to a stage of surface treatment with nitrogen prior to the pasteurisation, samples of 5 and 25% albumin subsequent to the pasteurisation and prior to quarantine, and samples of 5 and 25% albumin following the quarantine period, were analysed. FIG. 6 shows the results obtained, these being similar to those obtained in FIG. 4 for albumin at a concentration of 20%. There was observed the non-decrease in the HMA form and the non-increase in the HNA1 and HNA2 forms observed in FIGS. 2 and 3 with the method for the obtainment of the albumin of the prior art.

In addition to the analysis of the oxidative state, the measurement of the dissolved oxygen present in the samples following the surface treatment with nitrogen was made, the result being that in all cases the concentration of dissolved oxygen was equal to or less than 0.5 ppm.

Example 5: Method for the Obtainment of Albumin of the Present Invention Utilising a Stage of Surface Treatment with Helium Prior to the Pasteurisation The method for the obtainment of the albumin of the present invention corresponds to the method described in Example 1, including the stage described below. Following the obtainment of the sterile solution in the final container (FIG. 1, sterile filtration and filling stage), and having the objective of displacing the oxygen present in the air chamber remaining in the vial, the surface treatment with helium was carried out, inserting into the chlorobutyl stopper, and avoiding contact with the solution of albumin, two hypodermic needles (of the commercial type Braun Sterican 21G×1½", 0.80×40 mm, Germany, or similar) connected to two 0.22 μm PVDF filters (of the commercial type Millex GV Millipore, 0.22 μm, PVDF, 13 mm filter, USA, or similar), avoiding contact of the needles with the solution of albumin. One of the needles was destined as the inlet of the helium gas and the other as the outlet thereof having the objective of preventing overpressure within the container. The treatment with surface helium was carried out at room temperature for two hours, maintaining a constant flow of helium having the objective of permitting observation of the movement of the liquid within the container without it splashing within the same.

Having completed the surface treatment with helium, the method for the obtainment of albumin commencing from human plasma continued as described in Example 1 (FIG. 1, pasteurization in vials stage), until the obtainment of the final albumin product.

Figure 7:
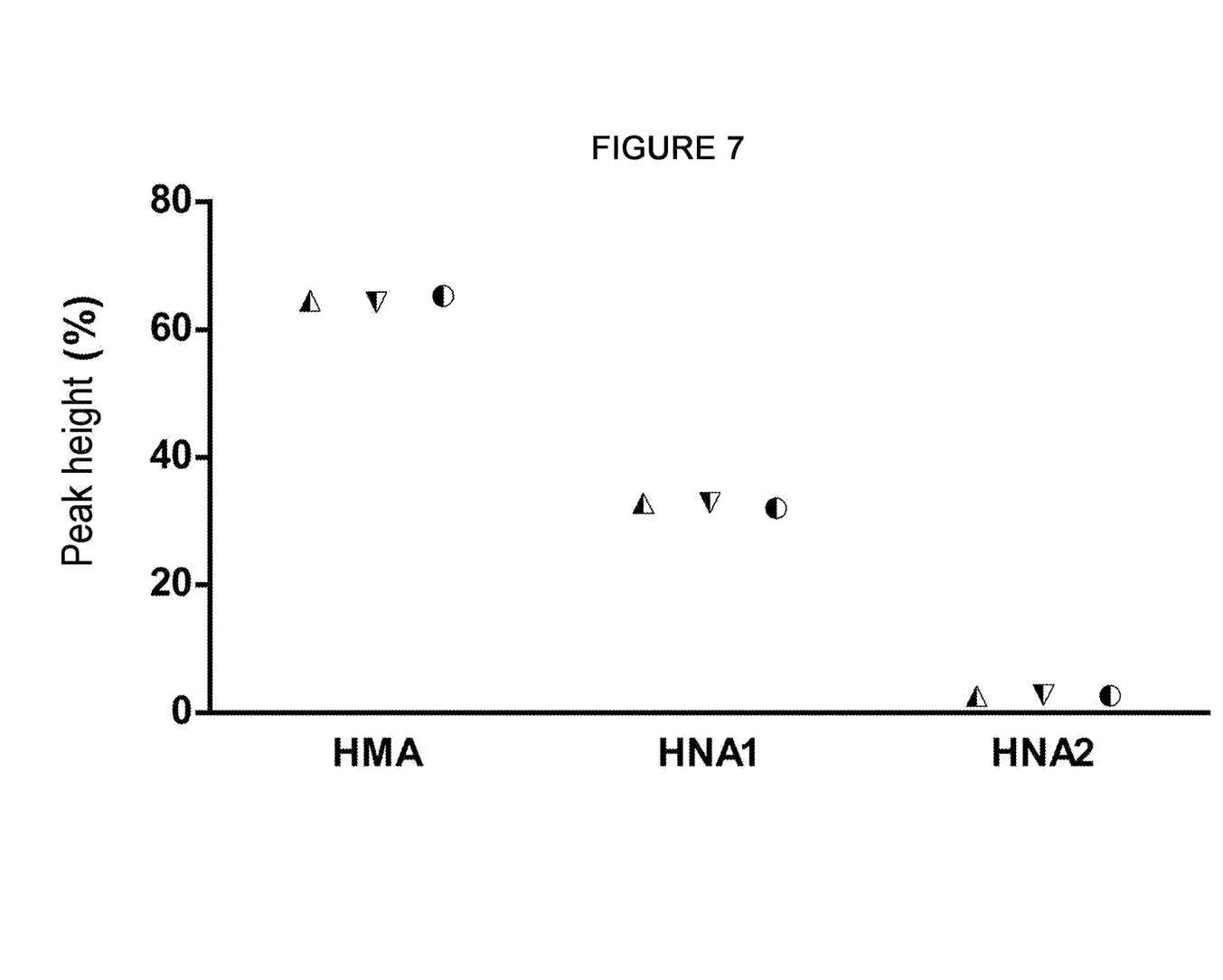
FIG. 7 shows a graph of the concentration of the HMA, HNA1 and HNA2 forms of Cys-34 of the albumin expressed as the height of the peak obtained by means of chromatography in various stages, utilising the method of the present invention wherein a stage of surface treatment with gaseous helium of the solution of albumin prior to the pasteurisation was used: (▲) sterile 25% solution of albumin and in final container (n=1); (▼) pasteurised 25% solution of albumin in final container and unquarantined (n=1); and (●) final 25% albumin product; wherein n represents the number of analysed batches.

In the same manner as in Examples 1 to 4, the oxidative state was analysed by means of anion exchange chromatography of the samples of albumin obtained with the technique of the present invention. Specifically, samples of albumin subjected to a stage of surface treatment with helium prior to the pasteurisation, samples of albumin following the pasteurisation and prior to quarantine, and samples of albumin following the quarantine period, were analysed. FIG. 7 shows the results obtained, these being similar to those obtained in FIGS. 4 and 6 utilising a stage of surface treatment with nitrogen prior to the pasteurisation, and also to those obtained in FIG. 5, utilising a stage of bubbling nitrogen into the solution prior to the pasteurisation. There was observed the non-decrease in the HMA form and the non-increase in the HNA1 and HNA2 forms observed in FIGS. 2 and 3 with the method for the obtainment of the albumin of the prior art.

In this case the measurement of the dissolved oxygen present in the samples following the treatment by bubbling helium was made, in the same manner as in Example 2, the result being that in all cases the concentration of dissolved oxygen was equal to or less than 0.5 ppm.

What is claimed is:

1. A method for the preparation of a solution comprising a human albumin, the method comprising: a stage of reducing a level of dissolved oxygen in the solution, wherein the level of dissolved oxygen is reduced to a concentration equal to or less than 0.5 ppm, wherein the solution has a final concentration of the human albumin between 4% and 25%, wherein about 50-69% of a total of the human albumin is in the form of human mercaptoalbumin (HMA), 27-42% is in the form of human non-mercaptoalbumin 1 (HNA1) and 3-5% is in the form of HNA2.

2. The method according to claim 1, wherein the stage of reducing the level of dissolved oxygen in the solution is carried out by a surface treatment of the solution with an inert gas.

3. The method according to claim 1, wherein the stage of reducing the level of dissolved oxygen in the solution is carried out by a bubbling of an inert gas into an interior of the solution.

4. The method according to claim 1, wherein the human albumin is of a plasmatic, recombinant origin or a transgenic origin.

5. The method according to claim 2, wherein the inert gas is nitrogen or helium.

6. The method according to claim 1, wherein the stage of reducing the level of dissolved oxygen in the solution is carried out prior to a stage of pasteurisation of the solution.

7. The method according to claim 1, wherein the stage of reducing the level of dissolved oxygen in the solution is carried out subsequent to a stage of pasteurisation of the solution.

8. The method according to claim 1, wherein subsequent to the stage of reducing the level of dissolved oxygen in the solution, the solution is maintained in an inert gas atmosphere.

9. The method according to claim 8, wherein the inert gas atmosphere is comprised of the inert gas nitrogen or helium.

10. The method according to claim 8, wherein the solution is packed and/or stored in a container comprising a material impermeable to oxygen.

11. The method according to claim 10, wherein the material impermeable to oxygen is glass.

* * * * *

UNITED STATES PATENT AND TRADEMARK OFFICE
CERTIFICATE OF CORRECTION

PATENT NO. : 10,350,274 B2
APPLICATION NO. : 14/724649
DATED : July 16, 2019
INVENTOR(S) : Juan Ignacio Jorquera Nieto et al.

Page 1 of 1

It is certified that error appears in the above-identified patent and that said Letters Patent is hereby corrected as shown below:

In the Specification

Column 3, Line 23, delete "homocystein" and insert --homocysteine--.

In the Claims

Column 10, Line 27, Claim 4, after "according" insert --to--.

Signed and Sealed this
Seventeenth Day of December, 2019

Andrei Iancu
*Director of the United States Patent and Trademark Office*